United States Patent
Xu et al.

(10) Patent No.: US 9,883,999 B2
(45) Date of Patent: Feb. 6, 2018

(54) METHOD FOR SOLUBILIZING RUTIN WITH POLYHYDROXY ALKYL ALCOHOLS

(71) Applicant: Colgate-Palmolive Company, New York, NY (US)

(72) Inventors: Shao Peng Xu, Guangzhou (CN); Wei Song, Guangzhou (CN); Xiong Fei Qin, Guangdong (CN); Yuan Hui Xie, Guangzhou (CN); Mahmoud Hassan, Somerset, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 15/106,478

(22) PCT Filed: Oct. 23, 2014

(86) PCT No.: PCT/US2014/062065
§ 371 (c)(1),
(2) Date: Jun. 20, 2016

(87) PCT Pub. No.: WO2015/094479
PCT Pub. Date: Jun. 25, 2015

(65) Prior Publication Data
US 2016/0338931 A1 Nov. 24, 2016

(30) Foreign Application Priority Data
Dec. 19, 2013 (CN) .......................... 2013 1 0703023

(51) Int. Cl.
*A61K 8/60* (2006.01)
*A61K 8/34* (2006.01)
*A61Q 11/00* (2006.01)

(52) U.S. Cl.
CPC .............. *A61K 8/602* (2013.01); *A61K 8/345* (2013.01); *A61Q 11/00* (2013.01); *A61K 2800/92* (2013.01)

(58) Field of Classification Search
CPC . A61K 8/42; A61K 8/463; A61K 8/34; A61K 8/345
USPC ....................................................... 424/48, 49
See application file for complete search history.

(56) References Cited

U.S. PATENT DOCUMENTS

| | | | | | |
|---|---|---|---|---|---|
| 3,992,519 | A | * | 11/1976 | Hofmann | A61K 8/42 424/48 |
| 5,578,307 | A | * | 11/1996 | Wunderlich | A61K 8/64 424/451 |
| 5,723,106 | A | * | 3/1998 | Buch | A61K 8/34 424/49 |

FOREIGN PATENT DOCUMENTS

| | | |
|---|---|---|
| CN | 1153174 A | 7/1997 |
| GB | 1308483 | 2/1973 |
| JP | S58-213706 | 12/1983 |
| JP | S60-208908 A | 10/1985 |
| JP | H04-24323 B2 | 4/1992 |
| WO | WO 02/047615 | 6/2002 |

OTHER PUBLICATIONS

"Anti-sunburn cosmetic composition contain rutin and ultraviolet absorbing agent deposited on surface of inorganic pigment," WPI World Patent Inf., Oct. 21, 1985.
International Search Report and Written Opinion mailed in International Application No. PCT/US2014/062065 dated Jan. 1, 2015.
Rodrigues et al., "Therapeutic potential of treatment with the flavonoid rutin after cortical focal ischemia in rats," Brain Research, Jan. 2013, 1503:53-61.
Suzuki et al., "Biochemical studies on the so-called vitamin P-like compound," J. Mie. Med. Coll., Jan. 1951, pp. 175-182.
Liu et al., 1991, Science of Chinese Patent Medicine, China Medical Science Press p. 120.

* cited by examiner

*Primary Examiner* — Walter Webb

(57) ABSTRACT

The present invention generally relates to oral care compositions which enhance the solubility of rutin comprising rutin and at least one polyhydroxyalkyl alcohol. The present invention also relates to methods for use and manufacturing said oral care compositions.

13 Claims, No Drawings

METHOD FOR SOLUBILIZING RUTIN WITH POLYHYDROXY ALKYL ALCOHOLS

CROSS-REFERENCE TO RELATED APPLICATIONS

This application is a United States National Application under 35 U.S.C. 371 of International Application PCT/US2014/062065, filed Oct. 23, 2014, which claims the benefit of Chinese patent application No. 201310703023.4, filed 19 Dec. 2013. The disclosures of the above applications are incorporated herein by reference.

BACKGROUND

Oral inflammation is associated with common oral conditions, including periodontitis, for example. Gingivitis is the initial stage of gum disease. A cause of gingivitis is plaque, which is a soft, sticky, colorless film of bacteria that forms on the teeth and gums. Plaque, if left untreated, produces toxins that can inflame or infect the gum tissue to cause gingivitis. Untreated gingivitis can eventually spread from the gums to the ligaments and bone that support the teeth, and can cause periodontitis. Rutin (IUPAC name: 2-(3,4-dihydroxyphenyl)-5,7-dihydroxy-3-[α-L-rhamnopyranosyl-(1→6)-β-D-glucopyranosyloxy]-4H-chromen-4-one; CAS no: 153-18-4) is a glycoside formed by the flavonol quercetin and the disaccharide rutinose and has the structure below:

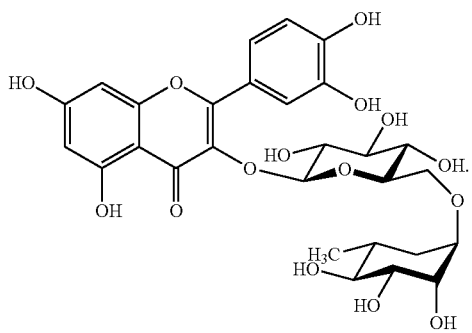

Rutin is found in a variety of plants, including rue (*Ruta graveolens*), mulberry leaf, *Houttuynia cordata* Thunb, *Sophora japonica* L., certain varieties of buckwheat, citrus, and apple. Rutin inhibits platelet aggregation and is believed to have anti-oxidant and anti-inflammatory properties. However, rutin is only poorly soluble in water (solubility ca. 13 mg/100 mL), and this property significantly restricts its delivery and effectiveness in oral care formulations. There is therefore a need in the art for oral care formulations which allow for the more effective delivery of rutin.

UK Patent No. 1,308,483 discloses preparations for the care of the teeth and the mouth. Example 2 of this document discloses a toothpaste comprising the sodium salt of the sulfuric acid ester of rutin in an amount of 0.20 wt % and glycerol (86%) in an amount of 10.00 wt %. It will be appreciated that the sulfuric acid ester of rutin discussed in the document has a different chemical structure to that of rutin itself.

U.S. Pat. No. 5,258,173 discloses a dentifrice composition comprising a stannous compound that releases stannous ions in the composition, such as stannous fluoride or stannous pyrophosphate. Rutin is identified as one of a series of antioxidants which may be included in the composition. No compositions comprising rutin are exemplified. The problem of improving the solubility of rutin in an oral care composition is not addressed by U.S. Pat. No. 5,258,173.

BRIEF SUMMARY

We evaluated rutin for use as an anti-gingivitis agent in toothpaste, e.g., to neutralize free radicals and so protect the oral membrane cells from oxidative damage, as well as to reduce inflammation. However, rutin proved difficult to formulate because it is hydrophobic and poorly soluble. As the oral environment is aqueous, effective delivery to the teeth is restricted. We have found that to be an effective antioxidant, rutin needs to be dissolved in the water phase. The more rutin dissolved in water phase, the stronger the anti-oxidation efficacy.

We experimented with a number of agents in efforts to enhance rutin's solubility, most of which proved ineffective. We surprisingly found, however, that the addition of one or more polyhydroxyalkyl alcohols, at particular ratios and concentrations, greatly increases the water solubility of rutin.

Accordingly, in one aspect the present invention relates to an oral care composition comprising rutin and at least one or more polyhydroxyalkyl alcohols. The polyhydroxyalkyl alcohol reduces the hydrophobicity of the rutin and helps it dissolve in water.

The present invention encompasses Composition 1.0, an oral care composition comprising rutin and at least one polyhydroxyalkyl alcohol wherein the ratio of the polyhydroxyalkyl alcohol to rutin by weight is at least 5:1, e.g., at least 10:1, for example 5:1 to 50:1, e.g., about 10:1.

For example, in various aspects the present invention encompasses:
1.1 Composition 1.0 wherein the composition is obtained or obtainable by forming a pre-mix comprising rutin and polyhydroxyalkyl alcohol, wherein the rutin is substantially dissolved in the pre-mix, then combining the pre-mix with the other ingredients in the composition.
1.2 Composition 1.1 wherein the polyhydroxyalkyl alcohol is selected from the group consisting of propylene glycol, sorbitol, glycerin and mixtures thereof.
1.3 Composition 1.1 or 1.2 wherein the ratio of polyhydroxyalkyl alcohol to rutin in the pre-mix is about 10:1.
1.4 Any foregoing composition, wherein the polyhydroxyalkyl alcohol comprises 100% propylene glycol.
1.5 Any of foregoing composition of 1.1 to 1.3 wherein the polyhydroxyalkyl alcohol comprises propylene glycol and glycerin wherein the ratio of propylene glycol to glycerin is selected from the ranges consisting of 10:90 to 90:10; 15:85 to 85:15, 15:85 to 25:75, 45:55 to 55:45, 85:15 to 75:25, 80:20, 50:50 and 20:80.
1.6 Any of foregoing composition of 1.1 to 1.3 wherein the polyhydroxyalkyl alcohol comprises propylene glycol and sorbitol wherein the ratio of propylene glycol to sorbitol is selected from ranges consisting of 70:30 to 90:10, 75:25 to 85:15 and 80:20.
1.7 Any foregoing composition wherein the amount of rutin in the composition is an amount effective to reduce inflammation and/or oxidative damage to the soft tissues in the mouth.
1.8 Any foregoing composition wherein the amount of rutin in the composition is 0.05-5%, e.g., 0.1 to 1%, e.g., about 0.5%.
1.9 Any foregoing composition, wherein the amount of solubilized rutin in the composition is at least 20% of the total rutin in the composition, e.g., wherein the amount of solubilized rutin is detectable in the composition by high performance liquid chromatography (HPLC), e.g., wherein the composition is diluted in water in a ratio of about 5:1 water to composition prior to carrying out the HPLC.

1.10 Any foregoing composition wherein the composition further comprises one or more additional botanical extracts, e.g., wherein the botanical extract is from a genus selected from the group consisting of *Origanum, Thymus, Lavandula, Salvia, Melissa, Cuminum, Petroselinum, Calendula, Tageles, Boswellia, Sambucus, Copaifera, Curcuma, Allium, Symphylum, Punica, Eulerpe, Sophora, Rheum, Fagopyrum, Camellia, Coplis, Hydraslis, Mahonia, Phellodendron, Berberis, Xanthorhiza, Lonicera, Vaccinium, Cinnamomum, VIZIS, Terminalia, Pinus, Albizia, Melia, Salvadora, Paullinia, Piper, Syzygium, Commiphora, Juglans, Sculellaria,* and *Magnolia.*

1.11 Any foregoing composition further comprising a compound selected from the group consisting of hesperetin, hesperidin, eriodictyol, quercetin, quercetagetin and quercetagitrin.

1.12 Any foregoing composition comprising an antibacterial agent selected from halogenated diphenyl ethers (e.g. triclosan) and herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract).

1.13 Any foregoing composition wherein the composition is prepared by forming a pre-mix comprising rutin and propylene glycol, wherein the rutin is substantially dissolved in the pre-mix, then combining the pre-mix with the other ingredients in the composition, wherein the pre-mix further comprises one or more poorly soluble agents, e.g., flavorings, antibacterial agents or botanical extracts, e.g., selected from the compounds as set forth in 1.7, 1.8, 1.9, 1.10, 1.11 or 1.12.

1.14 Any of the preceding compositions effective upon application to the oral cavity, e.g., with brushing, to reduce or inhibit gingivitis, to reduce or inhibit damage to the soft tissues in the mouth, and/or promote healing of sores or cuts in the mouth.

1.15 A composition obtained or obtainable by combining the ingredients as set forth in any of the preceding compositions.

1.16 Any of the preceding compositions wherein the composition is toothpaste or a mouthwash.

1.17 Any of the preceding compositions wherein the composition is a toothpaste optionally further comprising one or more of one or more of water, abrasives, surfactants, foaming agents, vitamins, polymers, enzymes, humectants, thickeners, antimicrobial agents, preservatives, flavorings, colorings and/or combinations thereof.

1.18 Any preceding composition wherein the composition is a toothpaste obtained or obtainable by the process of forming a pre-mix comprising rutin and polyhydroxyalkyl alcohol, wherein the rutin is substantially dissolved in the pre-mix, then combining the pre-mix with a toothpaste base, e.g., a toothpaste base comprising one or more of water, abrasives, surfactants, foaming agents, vitamins, polymers, enzymes, humectants, thickeners, antimicrobial agents, preservatives, flavorings, colorings and combinations thereof.

1.19 The process of paragraph 1.18, wherein the rutin and propylene glycol are mixed first and then followed by mixing with sorbitol.

The present invention also encompasses Method 2.0, a method to improve oral health in a subject in need thereof, e.g., to treat, reduce or inhibit gingivitis, to treat, reduce or inhibit damage to the soft tissues in the mouth, and/or to promote healing of sores or cuts in the mouth, the method comprising applying an effective amount of rutin in combination with propylene glycol, e.g., applying the oral composition of any of Compositions 1, et seq., to the oral cavity of a subject in need thereof.

In one aspect, the present invention provides the use of at least one polyhydroxyalkyl alcohol to enhance the solubility of rutin in an oral care formation. It has surprisingly been found that polyhydroxyalkyl alcohols may be used in oral care formulations to enhance the solubility of rutin. This allows for the more effective delivery of rutin to the oral cavity of a subject when the oral care composition is administered. The polyhydroxyalkyl alcohol may allow higher concentrations of rutin to be included in the oral care composition. In addition, improving the solubility of rutin may allow the oral care composition to be manufactured more easily, for example by preventing phase separation between the rutin and the remainder of the oral care composition. As used herein, enhancing the solubility of rutin means increasing the solubility of the rutin relative to its solubility in a comparative composition which does not comprise the polyhydroxyalkyl alcohol, and/or increasing the solubility of rutin relative to its aqueous solubility of 13 mg/100 mL.

Typically, the oral care composition will be a toothpaste, a tooth gel, a mouthwash, or the like. The oral care composition is most preferably a toothpaste. Optionally, the oral care composition is any of compositions 1.0 to 1.19 as defined above. In a further arrangement, the oral care composition is as defined in any one of claims 1 to 10.

Preferably, the use involves the use of a pre-mix in the manufacture of the oral care formulation. The pre-mix comprises rutin dissolved in at least one polyhydroxyalkyl alcohol. It is believed that forming a pre-mix in this manner helps to improve further the solubility of rutin in the oral care composition. The use of a pre-mix may allow the rutin to be dissolved more easily in the oral care composition, in comparison to adding the rutin directly. This may improve efficiency, e.g. by requiring less stirring.

Preferably, the polyhydroxyalkyl alcohol used is selected from propylene glycol, glycerin, and mixtures thereof. Propylene glycol, glycerin and mixtures thereof have been found to be surprisingly effective in improving the solubility of rutin. The use of propylene glycol is particularly advantageous.

When a mixture of propylene glycol and glycerin is used, the mixture preferably comprises at least 20% propylene glycol by weight of the mixture. More preferably, the mixture comprises at least 50% propylene glycol, and most preferably the mixture comprises at least 80% propylene glycol by weight of the mixture.

Alternatively, the polyhydroxyalkyl alcohol used may consist essentially of propylene glycol. In this arrangement, the propylene glycol may comprise water absorbed from the atmosphere and/or impurities arising from its manufacture or storage. In this arrangement, the propylene glycol is typically at least 95% pure, is preferably at least 99% pure, and is most preferably at least 99.8% pure.

In an embodiment, the invention provides the use of propylene glycol to enhance the solubility of rutin in an oral care formulation.

In another aspect, the present invention provides a method of manufacturing an oral care composition, which method comprises:

(a) dissolving rutin in a solvent to form a pre-mix; and
(b) combining the pre-mix with one or more further ingredients to form the oral care composition;
wherein the solvent comprises at least one polyhydroxyalkyl alcohol.

Preparing a pre-mix comprising rutin and a polyhydroxyalkyl alcohol allows the rutin to be efficiently incorporated into the oral care composition, and makes use of the surprisingly ability of polyhydroxyalkyl alcohols to solubilize rutin.

In step (a), rutin is dissolved in a solvent. This step typically involves mixing the rutin with the solvent, and stirring the resulting mixture. Suitably, the rutin is substantially fully dissolved in the solvent. In other words, the pre-mix will not be turbid and no undissolved rutin will be observable by visual inspection. The amount of rutin used may be selected such that the rutin substantially fully dissolves, i.e. such that the solubility limit of rutin in the solvent is not exceeded. One of skill in the art will be familiar with conventional methods of measuring solubility. For example, the solubility of rutin in a particular solvent may be measured by shake-flask with quantification by HPLC, UV/vis spectrometry, or any other conventional quantification method.

In step (b), the pre-mix is combined with one or more further ingredients to form the oral care composition. The nature of the further ingredients is not particularly limited and will vary depending on the oral care composition being prepared. The further ingredients will typically comprise an oral care active and an orally acceptable carrier. The oral care active may be any conventional oral care active, such as for example a fluoride source or an arginine source. One of skill in the art will be familiar with the orally acceptable carriers used in oral care compositions. Examples of ingredients which may be included in oral care compositions are provided in the detailed description. Any of the ingredients used in Compositions 1.0 et seq. may be used in the methods described herein.

The solvent comprises at least one polyhydroxyalkyl alcohol. The solvent may be a single polyhydroxyalkyl alcohol or a mixture of two or more polyhydroxyalkyl alcohols. Minor amounts of further components, such as water absorbed from the atmosphere, may be present in the solvent. Further components are most preferably absent, but may be present in an amount of less than 5%, preferably less than 2%, more preferably less than 1%, and still more preferably less than 0.1% by weight of the solvent. The solvent may consist essentially of a polyhydroxyalkyl alcohol or of a mixture of two or more polyhydroxyalkyl alcohols.

Preferably, the solvent is selected from propylene glycol, glycerin, and mixtures thereof. These materials have been found to be particularly useful in enhancing the solubility of rutin. Preferably, the solvent comprises at least 20% propylene glycol by weight of the solvent. Most preferably, the solvent consists essentially of propylene glycol.

Optionally, one or more further poorly soluble agents may be dissolved nit eh pre-mix in addition to the rutin. The poorly soluble agent may be, for example, a flavoring, an antibacterial agent, or a botanical extract. The botanical extract may be from a genus selected from *Origanum, Thymus, Lavandula, Salvia, Melissa, Cuminum, Pelroselinum, Calendula, Tageles, Boswellia, Sambucus, Copaifera, Curcuma, Allium, Symphylum, Punica, Eulerpe, Sophora, Rheum, Fagopyrum, Camellia, Coplis, Hydraslis, Mahonia, Phellodendron, Berberis, Xanthorhiza, Lonicera, Vaccinium, Cinnamomum, VlZlS, Terminalia, Pinus, Albizia, Melia, Salvadora, Paullinia, Piper, Syzygium, Commiphora, Juglans, Sculellaria*, and *Magnolia*. The antibacterial agent may be selected from halogenated diphenyl ethers (e.g. triclosan) and herbal extracts and essential oils (e.g., rosemary extract, tea extract, *magnolia* extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract).

Optionally, the oral care composition which is manufactured is any of compositions 1.0 to 1.19 as defined herein. Alternatively, the oral care composition which is manufactured is a composition as defined in any of claims 1 to 24.

Rutin may be present in the pre-mix in an amount of at least 5% by weight of the pre-mix. Preferably, the rutin is present in the pre-mix in an amount in the range 6% to 12% by weight of the pre-mix.

Optionally, the further ingredients introduced in step (b) comprise sorbitol. Sorbitol is useful as a humectant and a thickener, and may be used to form transparent gels. The inclusion of sorbitol in an oral care composition such as a toothpaste may improve the stability of the composition.

Optionally, the further ingredients are in the form of a toothpaste base composition. A toothpaste base composition may comprise one or more of water, abrasives, surfactants, foaming agents, vitamins, polymers, enzymes, humectants, thickeners, antimicrobial agents, preservatives, flavorings, colorings, and combinations thereof. In this arrangement, the oral care composition will be in the form of a toothpaste.

The method optionally includes the step of heating the solvent to a temperature in the range 50° C. to 70° C. The solvent may be heated before, during, or after the addition of the rutin to the solvent. Gentle heating accelerates the dissolution of the rutin while avoiding thermal decomposition of the rutin.

Optionally, in the arrangements where the solvent is heated, the pre-mix is allowed to cool before the pre-mix is combined with the further ingredients. For example, the pre-mix may be cooled to a temperature in the range of 16° C. to 32° C. before step (b). The pre-mix is preferably cooled to room temperature (e.g. to about 25° C.). It is not essential to cool the pre-mix before step (b).

Further optionally, the finished oral care composition comprises the pre-mix in an amount in the range 5% to 15% by weight of the composition. The amount of pre-mix is selected to optimize the stability of the oral care composition and the amount of dissolved rutin, and to optimize processing parameters. The use of a very large amount of pre-mix may reduce stability. The use of a very small amount of pre-mix would limit the amount of rutin delivered.

In some arrangements, the solvent is a mixture of a first polyhydroxyalkyl alcohol and a second polyhydroxyalkyl alcohol. The use of two different polyhydroxyalkyl alcohols in the same oral care composition may be desirable for providing oral care benefits, or for modifying process parameters, stability, product aesthetics, etc. It has surprisingly been found that the order of addition of the two polyhydroxy alcohols alters the solubility of rutin in the finished composition.

When the solvent is a mixture of a first polyhydroxyalkyl alcohol and a second polyhydroxyalkyl alcohol, the solubility of rutin in the first polyhydroxyalkyl alcohol being greater than in the second polyhydroxyalkyl alcohol, step (a) preferably comprises dissolving the rutin in the first polyhydroxyalkyl alcohol to form a solution and subsequently mixing the second polyhydroxyalkyl alcohol with the solution to form the pre-mix. By dissolving the rutin in the first polyhydroxyalkyl alcohol, it has surprisingly been found that the overall solubility of rutin in the final oral care compositions improved in comparison to a method wherein the first and second polyhydroxy alkyl alcohols are mixed before adding the rutin.

In this arrangement, the first polyhydroxyalkyl alcohol is preferably selected from propylene glycol and glycerin, and is most preferably propylene glycol. The second polyhydroxyalkyl alcohol may be sorbitol.

In one aspect the present invention relates in part to methods or processes for producing an oral care composition (e.g., toothpaste), e.g., according to any of Compositions 1.0, et seq., wherein the oral care composition comprises rutin and one or more polyhydroxyalkyl alcohol, comprising forming a pre-mix comprising rutin and one or more polyhydroxyalkyl alcohol, wherein the rutin is substantially dissolved in the pre-mix, then combining the pre-mix with the other ingredients in the composition. For example, in one embodiment, the process comprises

- combining rutin and one or more polyhydroxyalkyl alcohol;
- warming the combination comprising rutin and one or more polyhydroxyalkyl alcohol while mixing the combination, e.g. warming in a water bath at about 60° C. and mixing for about 10 minutes (e.g., using an IKA overhead mixer), to form a pre-mix;
- cooling the pre-mix, e.g., cooling down to approximately room temperature; and
- mixing the pre-mix with an oral care base, e.g., a toothpaste base.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

As used throughout, ranges are used as shorthand for describing each and every value that is within the range. Any value within the range can be selected as the terminus of the range.

As used herein, all measurement levels described herein are by weight of the total composition, unless otherwise indicated. Additionally, all references cited herein are hereby incorporated by reference in their entireties. However, in the event of a conflict between any definitions in the present disclosure and those in a cited reference, the present disclosure controls.

"Safe and effective amount" as used herein means a sufficient amount to treat the oral cavity, e.g., reduce plaque, gingivitis, and/or stain without harming the tissues and structures of the oral cavity.

As used herein, "cleaning" generally refers to the removal of contaminants, dirt, impurities, and/or extraneous matter on a target surface. For example, in the context of oral surfaces, where the surface is tooth enamel, the cleaning may remove at least some of a film or stain, such as plaque biofilm, pellicle or tartar.

The term "oral composition" is used herein to designate products which, in the ordinary course of usage, are retained in the oral cavity for a time sufficient to contact substantially all of the dental surfaces but are not intentionally ingested. Such products include, for example, dentifrices such as toothpaste and gels, mouthwashes, chewing gums and lozenges.

Various plant extracts contain the active compound rutin, which is believed to scavenge superoxide radicals, chelate metal ions, modulate bursts of neturophils, inhibit lipid peroxidation, maintain the biological antioxidant reduced glutathione, and reduce Fenton reactions (which generate reactive oxygen species). Thus, rutin has antioxidant, anti-inflammatory, anticarcinogenic, antithrombotic, cytoprotective and vasoprotective activities, which are beneficial for oral compositions.

As used herein, all percentages are by weight % of the total composition weight, unless otherwise indicated.

The oral compositions of the present invention (e.g., any of Compositions 1.0 et seq.) may also comprise a tooth whitening or tooth bleaching composition, which are known in the art. Suitable whitening and bleaching composition include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from about 1% to about 20% by weight based on the total weight of the composition, depending on the agent chosen.

The oral composition (e.g., any of Compositions 1.0 et seq.) optionally comprises an anti-calculus composition, such as, for example, one or more of the anti-calculus compositions discussed in U.S. Pat. No. 5,292,526 to Gaffar, et al. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus active can also include at least one water soluble, linear, molecularly dehydrated polyphosphate salt in an effective anticalculus amount. The anti-calculus active can also include a mixture of potassium and sodium salts, at least one of which is present in an effective anti-calculus amount as a polyphosphate anti-calculus agent. The anti-calculus active agent can also contain an effective anticalculus amount of linear molecularly dehydrated polyphosphate salt anti-calculus agent present in a mixture of sodium and potassium salts. The ratio of potassium to sodium in the composition can be up to less than 3:1. The polyphosphate can be present in the oral composition in various amounts, such as an amount wherein the weight ratio of polyphosphate ion to anti-bacterial agent ranges from in excess of 0.72:1 to less than 4:1, or wherein the weight ratio of the anti-bacterial enhancing agent to the polyphosphate ion ranges from about 1:6 to about 2.7:1, or wherein the weight ratio of the anti-bacterial enhancing agent to the polyphosphate ranges from about 1:6 to about 2.7:1. Other useful anticalculus agents include polycarboxylate polymers and polyvinyl methyl etherimaleic anhydride (PVM/MA) copolymers, such as GANTREZ®.

The oral care compositions of the invention (e.g., any of Compositions 1.0 et seq.) also may optionally comprise one or more chelating agents able to complex calcium found in the cell walls of the bacteria. Binding of this calcium weakens the bacterial cell wall, augments bacterial lysis, and reduces the formation of plaque. These anti-calculus agents may for example comprise a polyphosphate, e.g., pyrophosphate, tripolyphosphate, or hexametaphosphate, e.g., in sodium or potassium salt form. One group of chelating agents which may be useful in the present invention are soluble pyrophosphate salts. Pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition at least 0.1 wt. %, e.g., from about 0.5 wt. % to about 5 wt. %, about 1 wt. % to about 3 wt. %, or about 2%.

The oral care compositions of the invention (e.g., any of Compositions 1.0 et seq.) may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. An enzyme of a mixture of several compatible enzymes in the current invention constitutes about 0.002% to about 2.0% in one embodiment or about 0.05% to about 1.5% in another embodiment or in yet another embodiment about 0.1% to about 0.5%.

In preparing oral care compositions (e.g., any of Compositions 1.0 et seq.), it may be necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.05% to about 10% by weight of the total composition are used, e.g., from about 0.1% to about 7%, from about 0.5% to about 5%, or about 1%, 2%, or less than about 2%. Other thickeners for use in oral compositions include natural and synthetic gums and colloids, such as carrageenan (Irish moss), xanthan gum, sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. In some embodiments, the polymers may additionally promote delivery of active agents, and the such compositions may include polymers such as polyvinylmethyl ether maleic acid copolymers, e.g., as sold under the trade name Gantrez.

The oral care compositions of the invention (e.g., any of Compositions 1.0 et seq.) may also optionally include one or more surfactants, e.g., non-ionic, cationic or zwitterionic surfactants, or combinations thereof. For example, in some embodiments, the compositions may comprise at least one surfactant selected from sodium lauryl sulfate, cocamidopropyl betaine, and combinations thereof. In some embodiments, the compositions comprise an anionic surfactant, e.g. selected from the group consisting of: fatty acid monoglyceride monosulfates, higher alkyl sulfates (e.g., sodium lauryl sulfate); higher alkyl aryl sulfonates, (e.g., sodium linear dodecyl benzene sulfonate), higher olefin sulfonates (e.g., sodium higher olefin sulfonate), higher alkyl alkali sulfoacetates (e.g., sodium lauryl sulfoacetate); higher fatty acid esters of 1,2-dihydroxypropane sulfonates; the substantially saturated higher aliphatic acyl amides of lower aliphatic aminocarboxylic acid alkali metal salts, (e.g, having 12 to 16 carbon atoms in the fatty acyl radicals), higher alkyl poly-lower alkoxy (of 10 to 100 alkoxies) sodium sulfates, higher fatty acid sodium and potassium soaps of coconut oil and tallow. In some embodiments, the compositions may comprise an anionic surfactant, e.g., selected from sodium lauryl sulfate, sodium laureth sulfate, and mixtures thereof; e.g., may comprise sodium lauryl sulfate, in an amount from 0.5-3% by weight of the composition.

The compositions of the invention (e.g., any of Compositions 1.0 et seq.) may also include one or more flavoring agents or coloring agents known by those of skill in the art. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, *sassafras*, clove, sage, *eucalyptus*, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and optionally about 0.5 to about 1.5% by weight.

The present invention is further illustrated through the following non-limiting examples.

EXAMPLES

Example 1—Correlation of Rutin Level in Water Phase and its Anti-Oxidation Efficacy Rutin is dissolved in water to prepare a range of different levels of rutin solution. The protective efficacy of rutin solutions is measured using a cell staining method. In this method, the morphology of exfoliated human oral mucosal cells contacted with various concentrations of rutin is disclosed with Janus Green B dye. Photographic digital images are obtained using a light microscope with a 40× or 100× objective lenses connected to a digital camera. The color difference between the cell plasma and the area outside the cell, $\Delta E^*a,b$, is determined using the CIE $L^*a^*b^*$ system. The larger the $\Delta E^*a,b$ value, the stronger the protective efficacy. The method includes the following steps:

1. Human mucosal cells are collected and mixed with 1 mL Ringer solution, 0.5 mL $Fe^{2+}$ and 0.5 mL HAc—Ac buffer in a 5 mL Eppendorf tube.
2. The cell suspension is then equally divided into two tubes. To the first tube is added 0.2 mL of 20 mM $H_2O_2$. To the second tube is added 0.2 mL Ringer solution.
3. After 10 min, one drop of the above treated samples is placed on a microscope slide and stained with one drop of 0.1% Janus Green B for 1 h or longer.
4. After staining, the cells are observed under the light microscope. Digital images are also acquired and $\Delta E^*a,b$ is measured.

The results are as follows:

TABLE 1

Protective efficacy of rutin

| Rutin concentration (mM) | Protective efficacy (ΔE*a, b) |
|---|---|
| 0.5 | 5.5 |
| 1.0 | 24.7 |
| 2.0 | 38.9 |

These results show that the more rutin that is dissolved in water solution, the larger the ΔE*a,b value is, thus the stronger the anti-oxidation efficacy it can provide. Thus, it is not sufficient simply to add rutin to a toothpaste formulation. For the rutin to be effective, the formulation must provide optimal solubility for the rutin.

Initial evaluation of solubilizing agents is carried out by mixing rutin with different agents, and assessing whether the rutin dissolves, as seen by the relative clarity of the solutions. Propylene glycol (PG) is unexpectedly found to be the most effective solvent humectant to dissolve rutin. For example, among the polyol humectant materials evaluated—propylene glycol, PEG-40 hydrogenated castor oil, glycerin, PEG 600 and sorbitol—where 0.5% rutin is added to 10 g of each test solubilizer, the solubility capability of the humectants evaluated are ranked in the following order, with propylene glycol being the best and sorbitol being the worst.

propylene glycol>>glycerin>PEG600≈PEG-40 hydrogenated castor oil>sorbitol

Experiments are further designed to optimize humectant concentration for rutin solubility. Table 2 lists nine prototypes compounded from a pre-mix and a toothpaste base, where the pre-mix contains rutin and one or more of the propylene glycol, glycerin and sorbitol.

Pre-mixes are prepared by mixing the rutin with various solubilizing agents, as follows:
1) Formula amount of solubilizer(s) is added into container;
2) Formula amount of rutin is added into container with humectant;
3) Using a water bath at 60° C., contents are warmed and mixed for 10 minutes under constant stirring using an IKA overhead mixer;
4) After cooling the Pre-Mix down to room temperature, the contents are transferred to toothpaste mixer and mixed with toothpaste base for 10 minutes with ratios shown in Table 2.

TABLE 2

Formula design of humectants to solubilize rutin in Pre-Mix A

| Sample | Pre-Mix A | | | | Toothpaste Base % |
|---|---|---|---|---|---|
| | Rutin % | PG % | Sorbitol % | Glycerin % | |
| 1 | 0.5 | 5 | 0 | 0 | 94.5 |
| 2 | 0.5 | 4 | 1 | 0 | 94.5 |
| 3 | 0.5 | 2.5 | 2.5 | 0 | 94.5 |
| 4 | 0.5 | 1 | 4 | 0 | 94.5 |
| 5 | 0.5 | 0 | 5 | 0 | 94.5 |
| 6 | 0.5 | 4 | 0 | 1 | 94.5 |
| 7 | 0.5 | 2.5 | 0 | 2.5 | 94.5 |
| 8 | 0.5 | 1 | 0 | 4 | 94.5 |
| 9 | 0.5 | 0 | 0 | 5 | 94.5 |

Table 3 illustrates the toothpaste base formulation for the toothpaste comprising a rutin pre-mix as described in Table 2.

TABLE 3

| | Ingredient | Formula |
|---|---|---|
| Base Formula | Glycerin | 11.5 |
| | Sorbitol | 21.52 |
| | CMC 2000S (carboxymethylcellulose) | 0.5 |
| | Xanthan Gum | 0.3 |
| | Sodium Saccharin | 0.2 |
| | Sodium Fluoride | 0.22 |
| | Citric Acid Monohydrate | 0.6 |
| | Trisodium citrate dihydrate | 3.0 |
| | Zeodent ® 114 (Synthetic amorphous silica) | 20.0 |
| | Silica DT267 | 2.0 |
| | Flavor | 1.0 |
| | SLS (sodium lauryl sulfate) | 2.0 |
| | PVP (polyvinylpyrrolidone) | 2.0 |
| | water | 29.66 |
| Premix | Rutin Pre-Mix | 5.50 |
| | Total | 100.00 |

Example 2

Soluble rutin in the final formulations is assessed by high performance liquid chromatography using a) HPLC Equipment with an auto-sampler (Waters 2695): b) Column: Agilent Zorbax SB-CN, C 18, 5 μm, 250×4.6 mm; and c) UV Detector Waters 2489. Test conditions are as follows: a) Mobile phase: Methanol/H₂O/H₃PO₄ (550:450:1.8); b) Flow rate: 1 ml/min; c) Detection wavelength: 256 nm d) Run Time: 12 minutes. The procedure is as follows: a) Place 5 g toothpaste sample in glass beaker, add 5 ml water and stir for 30 minutes; b) Transfer the slurry to centrifugal tube and dilute to 25 ml with water, and centrifuge for 5 mins (8000 rpm); c) Filtrate and run through HPLC.

Table 4 demonstrates that toothpaste compositions with propylene glycol (PG) exhibit a higher concentration of soluble rutin in the toothpaste composition. Compositions comprising propylene glycol and glycerin also exhibit a higher concentration of soluble rutin as compared to compositions that comprise only glycerin or sorbitol. The best solubility is seen with for pre-mixes with 5% glycerin or 5% sorbitol, but the detectable soluble rutin is only found to be 0.08% and 0.04% respectively.

In the combination of propylene glycol with glycerin or sorbitol, results show that the higher the propylene glycol content in the formula, the higher the soluble rutin in the toothpaste. The introduction of sorbitol to propylene glycol during pre-mixing substantially decreases the solubility of rutin.

TABLE 4

Soluble rutin testing result in toothpaste (by HPLC method)

| Sample | Pre-Mix A | | | | Toothpaste Base % | Rutin detected % |
|---|---|---|---|---|---|---|
| | Rutin % | PG % | Sorbitol % | Glycerin % | | |
| 1 | 0.5 | 5 | 0 | 0 | 94.5 | 0.17 |
| 2 | 0.5 | 4 | 1 | 0 | 94.5 | 0.08 |
| 3 | 0.5 | 2.5 | 2.5 | 0 | 94.5 | 0.04 |
| 4 | 0.5 | 1 | 4 | 0 | 94.5 | 0.04 |
| 5 | 0.5 | 0 | 5 | 0 | 94.5 | 0.04 |
| 6 | 0.5 | 4 | 0 | 1 | 94.5 | 0.16 |
| 7 | 0.5 | 2.5 | 0 | 2.5 | 94.5 | 0.14 |
| 8 | 0.5 | 1 | 0 | 4 | 94.5 | 0.12 |
| 9 | 0.5 | 0 | 0 | 5 | 94.5 | 0.08 |

Example 3

It has been found that the solubility of rutin in an oral care composition comprising two polyhydroxyalkyl alcohols may be improved by optimizing the manufacture of the pre-mix. The solubility of rutin in an oral care composition comprising propylene glycol and sorbitol may approach the solubility of rutin in a composition without sorbitol if the rutin is dissolved in the propylene glycol before sorbitol is settled.

To illustrate this, a further sample (Sample 10) was prepared as follows:
1) The formula amount of propylene glycol was added into a container;
2) The formula amount of rutin was added into the container with the propylene glycol humectant;
3) The contents of the container were warmed using a water bath at 60° C. and mixed for 10 mins under constant stirring using an IKA overhead mixer;
4) The formula amount of sorbitol was added into container and mixed for an additional 5 minutes;
5) After cooling the pre-mix down to room temperature, the contents were transferred to a toothpaste mixer and mixed with the toothpaste base for 10 minutes.

The amount of soluble rutin present in Sample 10 was then determined using the method described in Example 2.

Table 5 demonstrates that the order of addition with respect to sorbitol results in a 75% increase in the amount of rutin detected (0.14−0.08/0.08×100%=75%).

TABLE 5

Soluble rutin testing result in toothpaste (by HPLC method) - different addition sequences

| | Pre-Mix A | | | | Toothpaste | Rutin |
|---|---|---|---|---|---|---|
| Sample | Rutin % | PG % | Sorbitol % | Glycerin % | Base % | detected % |
| 2 | 0.5 | 4 | 1 | 0 | 94.5 | 0.08 |
| 10 | 0.5 | 4 | 1 | 0 | 94.5 | 0.14 |

As those skilled in the art will appreciate, numerous changes and modifications may be made to the embodiments described herein without departing from the spirit of the invention. It is intended that all such variations fall within the scope of the appended claims.

What is claimed is:

1. An oral care composition comprising (a) a premix consisting of rutin dissolved in at least one polyhydroxyalkyl alcohol selected from propylene glycol or propylene glycol and glycerin, wherein the ratio of the polyhydroxyalkyl alcohol to rutin by weight is from 5:1 to 50:1; and (b) an oral care base comprising glycerin and sorbitol,
    wherein the oral care composition comprises from 5-15% of the premix, by weight of the composition;
    wherein the premix comprises 6-12% rutin, by weight of the premix; and
    wherein the oral care composition comprises 0.05-5% rutin, by weight of the oral care composition.

2. The oral care composition according to claim 1 wherein the at least one polyhydroxyalkyl alcohol is a mixture of propylene glycol and glycerin.

3. The oral care composition according to claim 1 wherein the at least one polyhydroxyalkyl alcohol consists essentially of propylene glycol.

4. The oral care composition according to claim 2 wherein the at least one polyhydroxyalkyl alcohol comprises propylene glycol and glycerin wherein the ratio of propylene glycol to glycerin by weight is selected from 10:90 to 90:10; 15:85 to 85:15, 15:85 to 25:75, 45:55 to 55:45, 85:15 to 75:25, 80:20, 50:50 and 20:80.

5. The oral care composition according to claim 4, wherein the ratio of propylene glycol to glycerin by weight is 10:90 to 90:10.

6. The oral care composition according to claim 5, wherein the ratio of propylene glycol to glycerin by weight is 85:15 to 75:25.

7. The oral care composition according to claim 1, wherein the ratio of the at least one polyhydroxyalkyl alcohol to rutin is about 10:1.

8. The oral care composition according to claim 1 wherein the amount of rutin in the composition is 0.1-1%.

9. The oral care composition according to claim 1 wherein the composition is a toothpaste optionally further comprising one or more of water, abrasives, surfactants, foaming agents, vitamins, polymers, enzymes, thickeners, antimicrobial agents, preservatives, flavorings, colorings and/or combinations thereof.

10. A method to improve oral health in a subject in need thereof comprising applying an effective amount of the oral care composition of claim 1 to the oral cavity of a subject in need thereof to reduce inflammation, to reduce oxidative damage to the soft tissues in the mouth, and/or to promote healing of sores or cuts in the mouth.

11. The method of claim 10, wherein the inflammation reduced is gingivitis.

12. A method of manufacturing an oral care composition, wherein the oral care composition is as defined in claim 1, wherein the method comprises:
    (a) dissolving rutin in a solvent to form a pre-mix; and
    (b) combining the pre-mix with one or more further ingredients to form the oral care composition;
    wherein the solvent comprises at least one polyhydroxyalkyl alcohol.

13. A method for producing the oral care composition of claim 3, comprising forming a pre-mix comprising rutin and propylene glycol, wherein the rutin is substantially dissolved in the pre-mix, then combining the pre-mix with sorbitol and the other ingredients in the composition.

\* \* \* \* \*